US00PP16791P3

(12) United States Plant Patent
Lintott

(10) Patent No.: US PP16,791 P3
(45) Date of Patent: Jul. 11, 2006

(54) *CHRYSANTHEMUM* PLANT NAMED 'WHITE LIGHTS'

(50) Latin Name: *Chrysanthemum morifolium*
Varietal Denomination: White Lights

(75) Inventor: Keith G. Lintott, Bognor Regis (GB)

(73) Assignee: Cleangro, Ltd, Chichester (GB)

( * ) Notice: Subject to any disclaimer, the term of this patent is extended or adjusted under 35 U.S.C. 154(b) by 48 days.

(21) Appl. No.: 11/055,173

(22) Filed: Feb. 9, 2005

(65) Prior Publication Data

US 2005/0177910 P1 Aug. 11, 2005

Related U.S. Application Data

(60) Provisional application No. 60/543,819, filed on Feb. 11, 2004.

(51) Int. Cl.
*A01H 5/00* (2006.01)

(52) U.S. Cl. ..... Plt./294

(58) Field of Classification Search ..... Plt./294
See application file for complete search history.

(56) References Cited

U.S. PATENT DOCUMENTS

PP10,218 P 1/1998 Pieters ..... Plt./82.1

*Primary Examiner*—Anne Marie Grunberg
*Assistant Examiner*—Annette H Para
(74) *Attorney, Agent, or Firm*—Winston & Strawn, LLP

(57) ABSTRACT

A new variety of *Chrysanthemum* plant named 'White Lights,' having a domed capitulum of white anemone flowers and a round shape. A very uniform flowering response habit.

1 Drawing Sheet

Latin name of the genus and species: Botanical classification: *Chrysanthemum morifolium.*

Variety denomination: The new *Chrysanthemum* variety denomination is 'White Lights.'

BACKGROUND OF THE INVENTION

The present invention comprises a new and distinct cultivar of *Chrysanthemum* botanically known as *Chrysanthemum morifolium,* and referred to by the variety name 'White Lights.'

'White Lights,' identified as 31183-0, originated from a cross-made in a controlled breeding program in Chichester, West Sussex, United Kingdom.

The female parent of the new *Chrysanthemum* variety is an undistributed, unpatented seedling identified as '30425-0.' The male parent of the new *Chrysanthemum* variety is an undistributed, unpatented seedling identified as '31310-0.' The new *Chrysanthemum* variety 'White Lights' has been asexually reproduced by vegetative cuttings in Chichester, West Sussex, United Kingdom and the distinguishing characteristics are retained through successive generations of asexual reproduction.

BRIEF SUMMARY OF THE INVENTION

'White Lights' is a garden type of *Chrysanthemum* plant variety having a domed-round plant form with white anemone type flowers.

Comparison with Female Parent

Plants of the new *Chrysanthemum* variety 'White Lights' are similar to the parent variety '30425-0' in plant habit and growth rate. However, in side-by-side comparisons in Chichester, West Sussex, United Kingdom, under commercial practice, plants of the new *Chrysanthemum* variety 'Foot Lights' differed from plants of the parent variety '30425-0' in the following characteristics.

1. The new *Chrysanthemum* variety 'White Lights' produces white anemone type flowers whereas the parent variety '30425-0' produces white single type flowers.
2. Plants of the new *Chrysanthemum* variety 'White Lights' have larger and longer inflorescence than plants of the parent variety '30425-0.'

Comparison with Male Parent

Plants of the new *Chrysanthemum* variety 'White Lights' are similar to the parent variety '31310-0' in plant habit and growth rate. However, in side-by-side comparisons in Chichester, West Sussex, United Kingdom, under commercial practice, plants of the new *Chrysanthemum* variety 'White Lights' differ from plants of the parent variety '31310-0' in the following characteristics.

1. The new *Chrysanthemum* variety 'White Lights' produces white anemone type flowers whereas the variety '31310-0' produces pink anemone type flowers.

Comparison with Other Variety

Plants of the new *Chrysanthemum* variety 'White Lights' differ from the variety 'Pidoul' (U.S. Plant Pat. No. 10,218). In side-by-side comparisons in Chichester, West Sussex, United Kingdom, under commercial practice, plants of the new *Chrysanthemum* variety 'White Lights' differed from plants of the variety 'Pidoul' in the following characteristics.

1. The new *Chrysanthemum* variety 'White Lights' produces white anemone type flowers whereas the variety 'Pidoul' produces white single type flowers.
2. The new *Chrysanthemum* variety 'White Lights' is less vigorous than the variety 'Pidoul.'
3. The new *Chrysanthemum* variety 'White Lights' has a faster natural season response than the variety 'Pidoul.'

BRIEF DESCRIPTION OF ILLUSTRATION

Typical specimens of the plant and flowers for the new *Chrysanthemum* 'White Lights' are shown in the accompanying digital photograph. The colors shown are as true as possible within the usual limits of this kind of illustration.

FIG. 1 is a whole plant view of the new variety 'White Lights' grown in a pot. The plant shown in the illustration is 63 days from the commencement of planting outdoors in mid-June.

DETAILED BOTANICAL DESCRIPTION

The following description of the new *Chrysanthemum* variety 'White Lights' is of plants grown outside, natural season, in Chichester, West Sussex, United Kingdom in the month of June. The variety has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new *Chrysanthemum* variety have been grown successfully under temperature conditions averaging about 50° F. at night and about 60° F. to 75° F. during the day under natural light conditions. The plants were grown outdoors in mid-June in 4 liter pots using loamless compost. No growth retardants were used. To produce a commercial product the plants may be pinched once with the center bud removed. The typical container size for commercial growth is 4 liter (8"). It has been observed that the shelf life of the new variety is about 26 days with a response time of about 9 weeks natural season. The new variety is suitable for growth in a temperature range of 50° F. to 75° F.

The new *Chrysanthemum* variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed-Round.
Height: 38 cm–53 cm.
Width: 0 cm–50 cm.
Branching characteristics: Free branching and spreading.
Length of lateral branches: 15 cm–28 cm.
Number of breaks from pinch: 7–15.
Stem:
- *Length.*—8 cm–9 cm.
- *Diameter.*—0.5 cm–0.7 cm.
- *Texture.*—Rough.
- *Color.*—Near 138A.

Response time: Near 9 weeks natural season.
Vigor: Medium.
Shelf life: Near 26 days.
Disease (susceptibility/resistance observed): None observed to date.
Pest (susceptibility/resistance observed): None observed to date.
Drought and temperature (susceptibility/resistance observed): None observed to date.
Growth retardant type and treatment: No treatment necessary.
The plants were grown for 9 weeks in natural season conditions.
Propagation:
- *Type.*—Vegetative Propagation via Stem Cuttings.
- *Time to rooting.*—12 days with soil temperatures of 70° F.
- *Rooting habit.*—Fine and Fibrous.

Foliage

Number of leaves per lateral branch: 9–15.
Compound or single: Single.
Arrangement of leaves: Alternate.
- *Shape of leaf.*—Typically 5 lobed ovate.
- *Size of leaf.*—Width: 1.5 cm–2.5 cm; Length: 2.5 cm–3.5 cm.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Slightly pubescent. Bottom: Slightly pubescent.

Petiole:
- *Color.*—Near 138B.
- *Length.*—0.6 cm–1.0 cm.

Venation: Net. Prominent mid vein at underside.
- *Color.*—Upper side: near 144B. Under side: near 144B.

Color:
- *Mature leaf, upper side.*—Near 139B; under side: near 139C.
- *Young leaf, upper side.*—Near 139B; under side: near 139B.

Flower

Flower appearance: Matte.
Flower type: Anemone.
Flower form: Flat.
Flower shape: Round.
Flowering habit: Cyme.
Number of blossoms per branch: 9–15.
Inflorescence form: Corymbiform.
- *Depth of fully expanded blossoms.*—0.8 cm–1.0 cm.
- *Diameter of fully expanded blossoms.*—2.5 cm–4.5 cm.
- *Anemone center diameter.*—1 cm–1.5 cm.

Phyllaries:
- *Number.*—22–25.
- *Color.*—Near 137C.
- *Length.*—0.5 cm–0.8 cm.
- *Width.*—0.1 cm–0.3 cm.
- *Texture/appearance.*—Shiny/Slightly Pubescent.

Peduncle: Peduncle length is shortest at the terminal flower and progressively longer down the stem; longest length is on average 11 cm, shortest length is on average 4 cm.
- *Length.*—3 cm–12 cm.
- *Color.*—Near 137C.
- *Surface.*—Pubescent.
- *Habit.*—Slightly Curving.
- *Strength.*—Medium.

Ray florets:
- *Form/shape.*—Straight.
- *Texture/appearance.*—Matte.
- *Number per flower.*—20–25.
- *Length.*—1.0 cm–1.5 cm; Width: 0.3 cm–0.6 cm.
- *Apex.*—Round.
- *Base.*—Tubular.
- *Margin.*—Entire.

Disc florets:
- *Form/shape.*—Cylindrical.
- *Texture/appearance.*—Matte.
- *Number per flower.*—125–150.

*Length.*—0.3 cm–0.5 cm; Width: 0.1 cm–0.15 cm.
*Diameter of disc.*—0.8 cm.
Fragrance: Slight.
Flower bud (at onset of color):
*Length.*—0.2 cm–0.4 cm.
*Diameter.*—0.3 cm–0.5 cm.
*Form/shape.*—Round/Slightly Flat.
General flower color:
1. *Ray florets, upper side.*—Immature: near 155B. Mature: near 155D. Older/Fading: near 65D.
2. *Ray florets, under side.*—Immature: near 155B. Mature: near 155D. Older/Fading: near 65D.
3. *Disc florets.*—Immature: near 14B. Mature: near 14C. Older/Fading: near 14D.
4. *Bud.*—Near 20C.

Flower progression with age; Flowers retain their color with age though some produce a pale pink tinge.
Lastingness of blooms is about 26 days.

Reproductive Organs

Gynoecium present on Ray and Disc florets.
Ray florets per individual flower:
*Pistil number.*—20–25 observed.
*Stigma color.*—Near 144D.
*Stigma shape.*—Forked.
*Style color.*—Near 144D.
*Style length.*—0.1 cm–0.3 cm.
Disc florets per individual flower:
*Pistil number.*—20–130 observed.
*Stigma color.*—Near 144D.
*Stigma shape.*—Forked.
*Style color.*—Near 144D.
*Style length.*—0.1 cm–0.2 cm.
Androecium present on Disc florets only.
Disc florets per individual flower:
*Stamen number.*—25–30 observed.
*Anther shape.*—Clubbed.
*Anther color.*—Near 14C.
*Pollen color.*—Near 12A.
*Pollen quantity.*—Small.
Fruit and seeds: None observed.

What is claimed is:

1. A new and distinct variety of *Chrysanthemum* plant, substantially as described and illustrated herein.

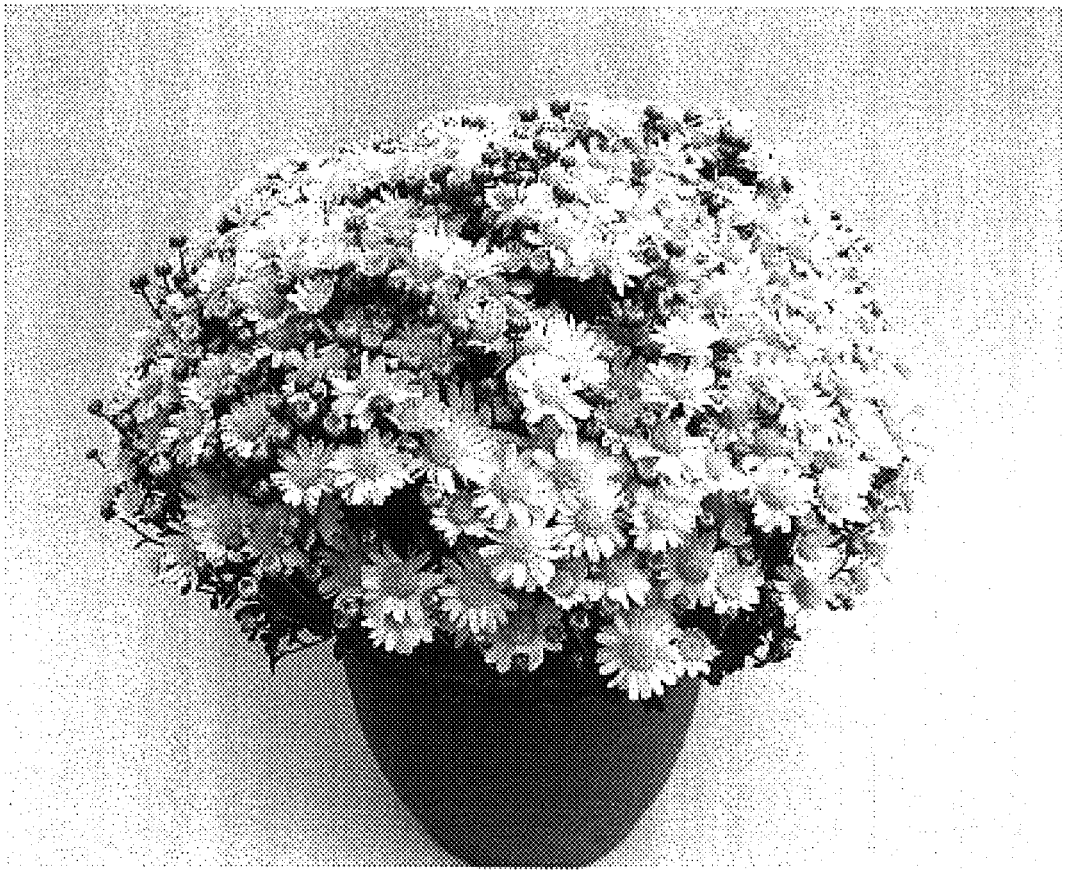

* * * * *